United States Patent [19]
Wolfbeis et al.

[11] Patent Number: 5,981,746
[45] Date of Patent: Nov. 9, 1999

[54] LUMINESCENCE INDICATOR

[75] Inventors: Otto S. Wolfbeis; Jörg Daub; Thomas Gareis; Matthias Kollmannsberger, all of Regensburg; Stefan Heinl, Neutraubling; Tobias Werner, Regensburg; Christian Huber, Abensberg, all of Germany; Andrei Boila-Göckel; Marco Jean Pierre Leiner, both of Graz, Austria

[73] Assignee: AVL Medical Instruments, Schaffhausen, Switzerland

[21] Appl. No.: 09/085,219

[22] Filed: May 27, 1998

[30] Foreign Application Priority Data

May 30, 1997 [AT] Austria ........................... 929/97

[51] Int. Cl.$^6$ ............ C07D 267/00; C07D 209/56; C07D 209/00
[52] U.S. Cl. ............ 540/450; 540/467; 548/110
[58] Field of Search ............ 48/110, 405; 540/450, 540/467

[56] References Cited

U.S. PATENT DOCUMENTS

| | | | |
|---|---|---|---|
| 4,774,339 | 9/1988 | Haugland et al. | 548/405 |
| 5,162,525 | 11/1992 | Masilamani et al. | 540/468 |
| 5,187,288 | 2/1993 | Kang et al. | 548/110 |
| 5,248,782 | 9/1993 | Haugland et al. | 548/110 |
| 5,274,113 | 12/1993 | Kang et al. | 548/405 |
| 5,433,896 | 7/1995 | Kang et al. | 252/700 |
| 5,439,828 | 8/1995 | Masilamani et al. | 436/74 |
| 5,451,663 | 9/1995 | Kang et al. | 530/367 |
| 5,516,911 | 5/1996 | London et al. | 548/236 |

OTHER PUBLICATIONS

B. Dietrich et al., Tetrahedron, vol. 29, pp. 1629–1645 (1973).

J.R. Lakowicz, "Topics in Fluorescence Spectroscopy", vol. 4: Probe Design and Chemical Sensing, pp. 133–134 (Plenum Press, New York and London) (1994).

Frank Kastenholz, Inaugural Dissertation, University of Cologne, Fig. 32, p. 54 (1993).

M.J.P. Leiner, P. Hartmann, "Theory and practice in optical pH sensing", Sensors and Actuators B, vol. 11, pp. 281–289 (1993).

A.P. de Silva, et al., Tetrahedron Letters, "A New Benzo–Annelated Cryptand and a Derivative with Alkali Cation–Sensitive Fluorescence", vol. 31, No. 36, pp. 5193–5196 (1990).

J.P. Dix, F. Vögtle, Chem. Ber. 113, 457–470 (1980).

CA 99:177723h.

*Primary Examiner*—Mukund J. Shah
*Assistant Examiner*—Pavanaram K Sripada
*Attorney, Agent, or Firm*—Baker & Botts LLP

[57] ABSTRACT

The invention relates to a compound having the general Formula I

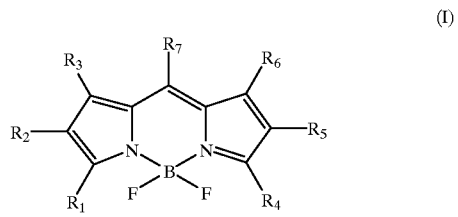

(I)

in which one of the groups $R_1$, $R_2$, $R_3$, $R_4$, $R_5$, $R_6$ and $R_7$ represents an ionophoric moiety and the remaining groups each independently are hydrogen, a lipophilic or hydrophilic group or a reactive group for coupling to a polymer or a biomolecule, or $R_2$ forms an aromatic ring system together with $R_3$ and $R_5$ forms an aromatic ring system together with $R_6$.

The compound of the invention is useful as a luminescence indicator for alkali ions.

8 Claims, 4 Drawing Sheets

LUMINESCENCE INDICATOR

BACKGROUND OF THE INVENTION

The present invention relates to luminescence indicators for determining cations, in particular alkali ions, of liquid, in particular aqueous, media. In effecting such determination, the substance to be determined (=analyte) is contacted with a luminescence indicator (=luminophore-ionophore) having a luminophoric moiety and an ionophoric moiety, which ionophoric moiety reacts with the analyte present in the sample, wherein the luminophoric moiety changes its luminescence properties, after which the luminescence is measured and the concentration and activity of the analyte are deduced, i.e. the cation is determined, utilizing the test reading.

A determination method of this type is based on the so-called "PET effect". This latter term denotes the transfer, induced by photons, of electrons (photoinduced electron transfer=PET) from the ionophoric moiety or ionophore, respectively, to the luminophoric moiety or luminophore, respectively, which leads to a decrease in the (relative) luminescence intensity and the luminescence decay time of the luminophore. Absorption and emission wavelengths, however, remain basically unaffected in the process (J. R. Lakowicz in "Topics in Fluorescence Spectroscopy", Volume 4: Probe Design and Chemical Sensing; Plenum Press, New York & London (1994)).

By the binding of ions to the ionophore, the PET effect is partly or completely inhibited, sb that there is an increase in the luminescence of the luminophoric moiety. Hence, the concentration or the activity of the ion to be determined can be deduced by measuring the change in luminescence properties, i.e. luminescence intensity and/or luminescence decay time.

From U.S. Pat. No. 5,516,911, fluorescence indicators for determining intracellular calcium are known which carry fluorescent substituents capable of acting as optical indicators.

A determination method is also known from U.S. Pat. No. 5,439,828, where diaza-cryptands are utilized as the luminophore-ionophore, which diaza-cryptands have been functionalized as fluorophores with fluorescent coumarins and, depending on their structure, are selective for lithium, sodium or potassium ions. It is stated that these luminophore-ionophores can be used in sample media of neutral pH and are even the preferred choice in such systems.

Yet, research (Frank Kastenholz, Inaugural Dissertation, University of Cologne, 1993, FIG. 32, p. 54) has shown that in the physiological pH range the fluorescence signal depends significantly on the pH of the sample and increases considerably with decreasing pH, even from pH 7.4 onwards. This affects the accuracy of a determination carried out in a biological sample. Moreover, the compounds that are being used have the disadvantage that the employed coumarins show absorption wavelengths of about 336 nm and hence cannot be excited by commercial LEDs.

These disadvantages also apply to the luminophore-ionophores mentioned in U.S. Pat. No. 5,162,525.

From Tetrahedron Letters, Volume 31, No. 36, pp. 5193–5196 (1990), diaza-cryptands are known in which the two nitrogen atoms are bound to a respective aromatic ring each, i.e. are aryl nitrogens and aniline-type nitrogens, respectively. Research conducted by the applicant has shown that these diaza-cryptands are not suited for determining potassium ions if they are present in the physiological range of concentration and at physiological pH values of the blood (7.0–7.6).

U.S. Pat. No. 4,774,339, U.S. Pat. No. 5,187,288, U.S. Pat. No. 5,274,113 and U.S. Pat. No. 5,248,782 describe fluorescent dyes containing dipyrrometheneboron difluoride as the parent substance and its derivatives with reactive substituents for covalent binding to biomolecules.

From U.S. Pat. No. 5,433,896, fluorescent dyes are known which contain 1-[isoindolyl]methylene-isoindiol as the parent substance.

Dye-conjugates of dipyrrometheneboron difluoride, wherein at least one of the reactive substituents covalently binds a dye molecule to a specific binding pair member, f.i. a nucleotide or a protein, are described in U.S. Pat. No. 5,451,663.

SUMMARY OF THE INVENTION

The present invention has as its object to make available luminophore-ionophores which lack significant dependence of the luminescence properties on the pH value of the sample at physiological pH values and thus are suited for determination in biological samples.

Further, the method of the invention is to be particularly well suited for practice in the presence of physiological concentrations of alkali ions, i.e. it should exhibit a strong dependence of the luminescent signal on the concentration of the alkali ion being determined.

This object is achieved in that the indicator that is used is a compound of the general Formula I

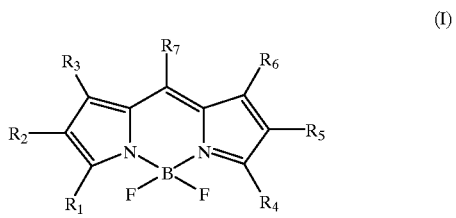

(I)

in which one of the groups $R_1$, $R_2$, $R_3$, $R_4$, $R_5$, $R_6$ and $R_7$ represents an ionophoric moiety and the remaining groups each independently are hydrogen, a lipophilic or hydrophilic group or a reactive group for coupling to a polymer or a biomolecule, or $R_2$ forms an aromatic ring system together with $R_3$ and $R_5$ forms an aromatic ring system together with $R_6$.

Suitable lipophilic groups would f.i. be substituted and unsubstituted alkyl groups and alkoxy groups having up to 20 C atoms.

Suitable hydrophilic groups would be alkyl groups having 1–17 C atoms and at least one hydroxyl group, and/or functional groups which at the pH of the measuring solution are present in a dissociated condition, such as f.i. carboxylic acids, sulfonic acids and phosphoric acids.

Reactive groups f.i. for coupling to aminofunctionalized polymers, f.i. aminocellulose and aminofunctional polyacrylamides, are known f.i. from U.S. Pat. No. 4,774,339, Table 4.

It is preferred that $R_7$ represent the ionophoric moiety and it is preferred that $R_3$ and $R_6$ be independently hydrogen or methyl.

It is preferred that the groups $R_1$ and $R_4$ represent a lipophilic group, in particular a tert. butyl each.

BRIEF DESCRIPTION OF THE DRAWINGS

Further objects and advantages of the present invention will be more fully appreciated from a reading of the detailed description when considered with the accompanying drawings wherein.

DETAILED DESCRIPTION OF THE PREFERRED EMBODIMENTS

Figure 1:
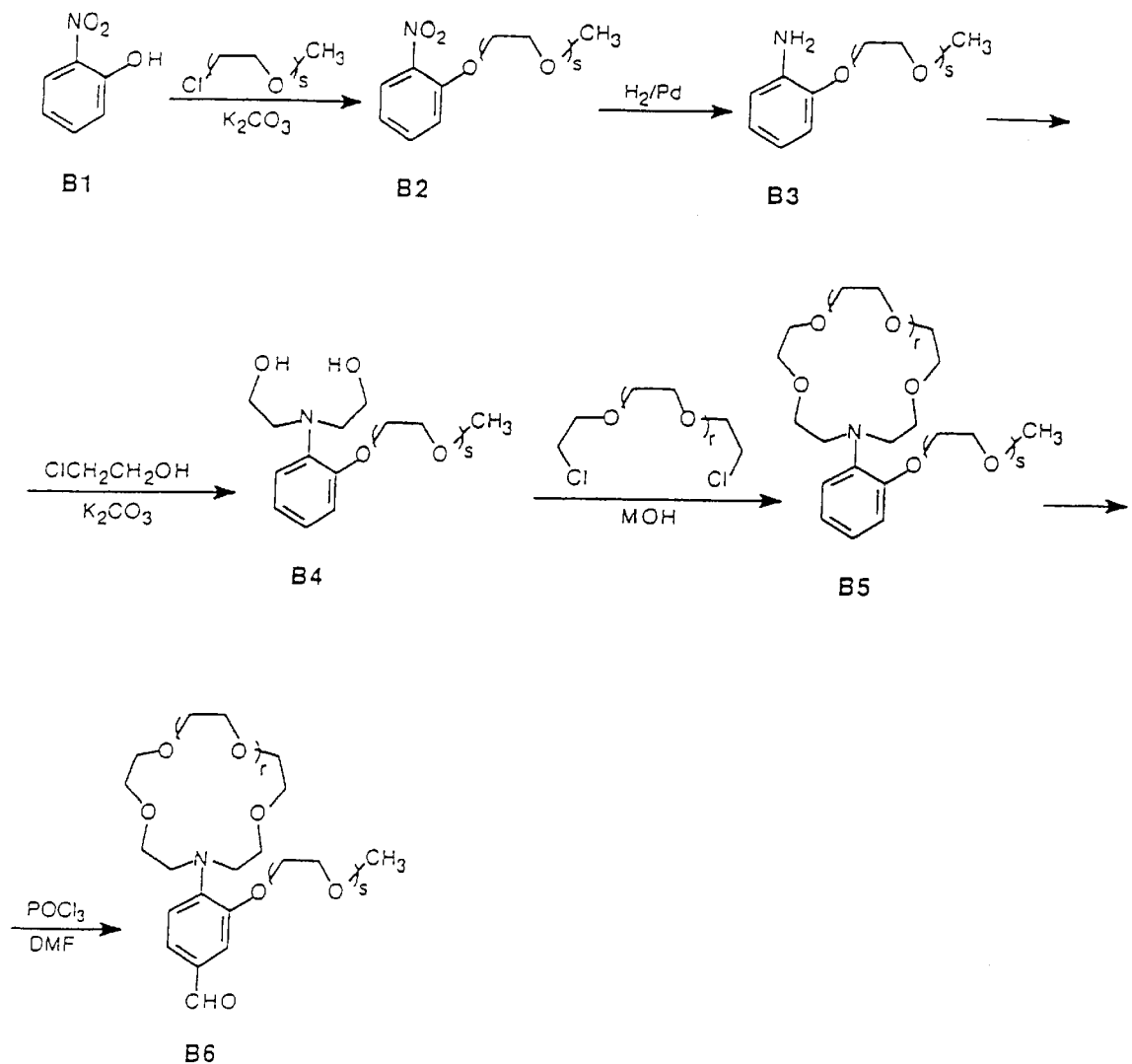
FIG. 1 is an illustration of a synthetic pathway for the monoaza-crown ether moiety of the ionophoric moiety in accordance with the invention.

The following substitution patterns are particularly preferred for the compound of the invention having the general Formula I:

Pattern 1:
$R_7$: ionophoric moiety;
$R_1$, $R_4$: lipophilic group, preferably t-butyl;
$R_3$, $R_6$: independently —$CH_3$ or H;
$R_2$ or $R_5$: acid group, preferably propionic acid group for immobilization;

Pattern 2:
$R_7$: ionophoric moiety;
$R_1$, $R_4$: lipophilic group, preferably t-butyl;
$R_3$: independently —$CH_3$ or H;
$R_6$: acid group, preferably propionic acid group for immobilization;

Pattern 3:
$R_7$: ionophoric moiety;
$R_1$: lipophilic group, preferably t-butyl;
$R_3$, $R_4$, $R_6$: independently —$CH_3$ or H;
$R_5$: acid group, preferably propionic acid group for immobilization.

In the compound of the invention of the general Formula I, it is preferred that the ionophoric moiety be a monoaza-crown ether having the general Formula II

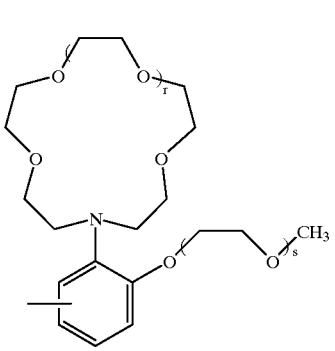

(II)

in which r and s independently mean the number 0, 1 or 2.

In the general Formula II, the horizontal line drawn on the benzene ring is intended to symbolize the covalent chemical bond through which the ionophoric moiety is bound directly to the compound of the general Formula I. That bond may be present in ortho position, the two meta positions or in para position to the nitrogen.

These new luminophore-ionophores have been found to be very useful for determining cations, especially alkali ions, at a physiological pH and at physiological concentrations.

Further, the monoaza-crown ethers of the invention have been found to be particularly useful for determining sodium ions in the concentration range between 110 and 180 mmol/l.

Suitable luminophoric moieties would be all those moieties by which in combination with the skeleton of the general Formula I a PET effect can be achieved. A great number of ionophoric moieties is known from literature which in combination with the ionophore give a PET effect or in principle are suited for this purpose. By coupling these known ionophoric moieties to the above skeleton of the general Formula I, new compounds are obtained which may be examined by the man skilled in the art in order to find out whether a PET effect can be obtained.

Those skilled in the art will be aware that in order for a PET effect to materialize it is essential in particular that the electron donor of the ionophoric moiety be electronically decoupled from the electronic system of the luminophoric moiety (skeleton of the general Formula I).

Electronic decoupling can be recognized f.i. from the fact that there is no significant change concerning the wavelengths of the absorption and emission spectra of the luminophoric moiety.

For determining sodium ions there is preferably utilized a monoaza-crown ether of the general Formula II in which r and s mean the numbers 1 and 0, respectively.

For determining potassium ions it is further preferred to utilize a monoaza-crown ether of the general Formula II in which r and s mean the numbers 2 and 1, respectively.

In the following, the invention will be described in greater detail by means of examples, wherein there will be explained the synthesis and properties of some preferred indicators. Other indicators in accordance with the invention can be prepared in analogous manner by the person skilled in the art.

1. Synthesis of precursors of the compounds of this invention:

1.1. Synthesis of the ionophoric moiety of the monoaza-crown ethers of the invention (FIG. 1)

The synthetic pathway for the ionophoric moiety of the monoaza-crown ethers of the invention is represented generally in FIG. 1

General Process (FIG. 1)

The synthesis of monoaza-crown (lariat) ethers with side-arms was through two main steps: alkylation and cyclization. It was feasible to alkylate 2-nitrophenol B1 in dimethylformamide in the presence of $K_2CO_3$ using chloroethyl-alkoxyethers of different chain lengths (s=0, 1, 2). The resulting nitro compounds B2 were hydrated to obtain amines B3, followed by alkylation of the amino group in chloroethanol with $K_2CO_3$ as the base to obtain the 2-[N, N-bis (2-hydroxyethylaminophenyl-alkoxyethyl-ethers B4 (s=0, 1, 2). These bis-hydroxy compounds B4 were cyclized with ethylglycol-dichloroethyl ethers (r=0, 1, 2) in dioxane containing alkali hydroxide to obtain the lariat ethers B5 (r=0, 1, 2; s=0, 1, 2). These ethers B5 (phenylaza-crown ethers) were formylated to obtain the intermediate products B6 (r=0, 1, 2; s=0, 1, 2).

Description of individual reaction steps of FIG. 1

N,N-bis (2-hydroxyethyl)-2-methoxyaniline B4 (s=0):

452 g (4 mol) of o-anisidine were dissolved in 1932 g (24 mol) 2-chloroethanol and heated at 80° C. for 15 min.

Subsequently, 608 g (4.4 mol) $K_2CO_3$ were added slowly in order to keep the temperature below 110° C. (exothermal reaction). The mixture was heated at 95° C. for 22 hours and was cooled down. About 800 ml unreacted chloroethanol were evaporated and the residue diluted with 1 l water and extracted twice with 1 l chloroform. The extract was washed 5 times with 1.5 l water and dried over $K_2CO_3$. The solvent was evaporated, wherein 404 g (yield: 48%) of light-brown oil were obtained. The thin-layer chromatogram showed a purity of about 95%.

$^1$H NMR (CDCl$_3$), δ (ppm): 3.18 (t, 4H), 3.50 (t, 4H), 3.60 (m, 2H), 3.82 (s, 3H), 6.90 (m, 2H), 7.10 (m, 1H), 7.19 (m, 1H).

2-methoxyphenylaza-15-crown-5 B5 (s=0, r=1):

This step was carried out based on J. P. Dix and F. Vögtle, Chem. Ber. 113, 457–470 (1980).

403 g (1.91 mol) B4 (s=0) were dissolved in 2210 ml dioxane and heated at 80° C. for 20 min. Subsequently, 168 g (4.20 mol) ground NaOH were slowly added within 3 hours. The temperature was raised to 95° C. when 300 ml (1.93 mol) bis (2-chloroethoxyethane) were added in one portion. Thereafter the reaction mixture was heated at 95° C. for 30 hours. After filtering the hot mixture the solvent was evaporated. The residue was treated with a solution of 234 g (1.91 mol) NaClO$_4$ in 640 ml methanol. The mixture was stirred for 30 min at 60° C. and was concentrated to about 300 ml. 860 ml ethylacetate were added, followed by stirring at room temperature for 20 min. The mixture was subsequently allowed to stand at room temperature for 2 hours.

The resulting precipitate was filtered, washed twice with 200 ml ethyl acetate and dried at room temperature for 30 min, wherein 199 g aza-crown sodium perchlorate complex were obtained as a soft white powder. This latter powder was dissolved in a mixture of 600 ml dichloromethane and 600 ml water, and the aqueous phase was again extracted with 400 ml dichloromethane. The organic layers were united, washed 8 times with 600 ml deionized water and dried over Na$_2$SO$_4$. The dichloromethane was evaporated, wherein 100.4 g of light-brown oil (yield: 16%) were obtained.

$^1$H NMR (CDCl$_3$), δ (ppm): 3.49 (t, 4H), 3.68 (t, 16H), 3.82 (s, 3H), 6.88 (m, 3H), 7.12 (m, 1H).

4-formyl-2-methoxyphenylaza-15-crown-5 B6 (s=0, r=1):

100 g (308 mml) B5 (s=0, r=1) were dissolved in 145 ml (1850 mmol) dimethylformamide in a 500 ml three-necked flask and cooled down to −5° C. 57.4 ml (616 mmol) POCl$_3$ were added dropwise in an addition funnel. The internal temperature of the flask was not allowed to rise above 5° C. This was followed by 16 hours of stirring at room temperature, pouring onto 500 g ice and adjustment to pH 7 with saturated aqueous $K_2CO_3$ solution. The solution was extracted twice with 500 m chloroform. The chloroform phase was washed twice with 500 ml water, then dried over 100 g MgSO$_4$ for 1 hour. The solvent was evaporated, wherein 85 g of light-yellow oil were obtained which crystallized when allowed to stand at room temperature overnight. Recrystallization from ethylacetate/hexane (1:4) yielded 56 g light-orange crystals (yield: 51%).

$^1$H NMR (CDCl$_3$), δ (ppm): 3.68 (t, 16H), 3.78 (t, 4H), 3.82 (s, 3H), 7.05 (m, 1H), 7.28 (m, 2H), 9.78 (s, 1H).

Figure 2:
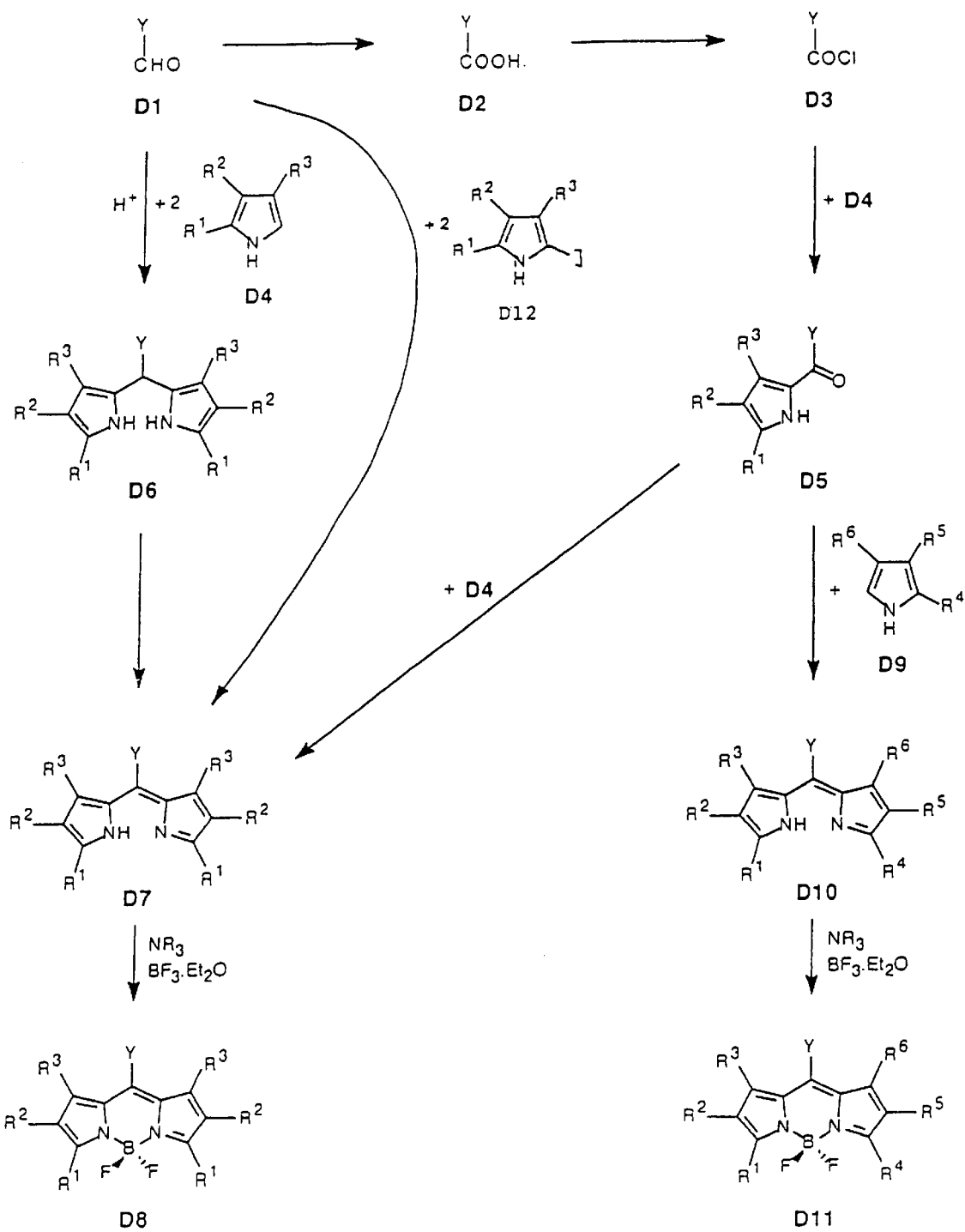
FIG. 2 is an illustration of a synthetic pathway for the preparation of compounds in accordance with the invention.

2. Synthesis of compounds of this invention 2.1. General Synthesis (FIG. 2)

2.1.1. Synthetic pathway 1 (symmetrically substituted derivatives D8)

An aldehyde D1 in which Y represents the ionophoric moiety of the general Formula (II) i.e. the compound B6, and the pyrrole derivative D4 were dissolved in an organic solvent and mixed with an acid, yielding the compound D6 as an intermediate product. By adding p-chloranil in an appropriate solvent, the compound D7 was obtained by oxidation of D6. In the case of the p-hydroxybenzaldehyde derivatives, the dipyrromethene D7 may be obtained directly from the reaction solution and may even be isolated.

Alternatively, the dipyrromethene D7 may also be prepared by reacting D1 with the iodine compound D 12.

Reaction of D7 in order to obtain the symmetrically substituted 4,4-difluoro-4-bora-3a,4a-diaza-s-indacene derivative D8 was effected by alternately adding ethyldiisopropylamine and BF$_3$.Et$_2$O to the reaction solution.

The reaction solution of D8 was washed with water, dried over magnesium sulfate and concentrated in vacuo. After repeated column chromatography on silica gel, the compound D8 of the invention was obtained which could be recrystallized from an appropriate solvent (f.i. chloroform/hexane).

2.1.2. Synthetic pathway 2 (symmetrically substituted derivatives D8)

The above aldehyde D1, in which Y represents the ionophoric moiety of the general Formula (II), was oxidized to give the carboxylic acid D2 and subsequently was converted into the corresponding acid chloride D3.

The acid chloride D3 obtained above was then reacted with the pyrrole derivative D4 to obtain the ketone D5, and through further reaction with D4, D7 was obtained. Conversion of D7 into D8 was effected in the manner already described.

The reaction solution of D8 was washed with water, dried over magnesium sulfate and concentrated in vacuo. After repeated column chromatography on silica gel, the compound D8 of the invention was obtained which could be recrystallized from an appropriate solvent (f.i. chloroform/hexane).

2.1.3. Synthetic pathway 3 (unsymmetrically substituted derivatives D11)

The ketone D5 obtained in the manner described above could be converted to D10 with a pyrrole derivative D9 other than D4. By adding ethyldiisopropylamine and BF$_3$.Et$_2$O to the reaction solution, the unsymmetrically substituted 4,4-difluoro-4-bora-3a,4a-diaza-s-indacene derivative D11 was obtained from D10.

The reaction solution of D11 was washed with water, dried over magnesium sulfate and concentrated in vacuo. After repeated column chromatography on silica gel, the compound D11 of the invention was obtained which could be recrystallized from an appropriate solvent (f.i. chloroform/hexane).

2.1.4. Synthesis of specific compounds
8-[4'-C-(aza-15-crown-5)-3'-methoxyphenyl]-3,5-methoxycarbonyl-ethyl-4-difluoroboron-3a,5a-s-indacene:

0.32 g (2 mmol) 2-pyrrole-methylpropionate and 0.35 g (1 mmol) 4-formyl-2-methoxyphenylaza-15-crown-5 (B6, s=0, r=0) were dissolved in 100 ml water-free $CH_2Cl_2$ and stirred for 5 min under a nitrogen atmosphere. 40 μl trifluoroacetic acid were added and the solution stirred for another 1.5 hours. Then, 0.94 g (2 mmol) tetrachlorobenzoquinone in 20 ml water-free tetrahydrofuran were added in one portion. The resulting dark red solution was stirred for 15 min. 5×1 ml diisopropylethylamine and 5×1 ml boron trifluoride diethyl etherate were added alternately. The mixture was stirred for 30 min and washed twice with 100 ml 2 N HCl, dried over $K_2SO_4$ and purified using silica gel 100 with 9:1 CHCl$_3$/ethylacetate, wherein 0.21 g of orange-colored powder were obtained.

General description of the hydrolysis of the diester D8 into dicarboxylic acids:

The diester D8 (Y=aza-crown B5 with s=0 and r=1) that was obtained was dissolved in tetrahydrofuran and diluted to double the volume with water. The mixture was acidified with concentrated $H_3PO_4$ and stirred at 70° C. for 4 days. This solution was concentrated in vacuo, the residue taken up in chloroform, dried over sodium sulfate and the solvent removed. The residue was then purified through column chromatography on silica gel with chloroform/methanol as the mobile phase. Also, monocarboxylic acid was obtained as a byproduct.

This luminescence indicator is useful for determining physiological concentrations of sodium ions.

Preparation of the monoesters: $R_1$=—$CH_2$—$CH_2$—COO—$CH_3$, $R_4$=—$CH_2$—$CH_2$—COOH, and of the diacids: $R_1$=$R_4$—$CH_2$—$CH_2$—COOH:

The orange-colored powder obtained in the two previous examples of synthesis was dissolved in 4 ml tetrahydrofuran and then diluted with 6 ml water. Then, 0.3 ml 85% $H_3PO_4$ were added, followed by 4 days of heating at 70° C. The tetrahydrofuran was evaporated and the residue extracted twice with 50 ml chloroform and dried over $K_2SO_4$. The solvent was evaporated, yielding 0.17 g oil. This oil was purified using a column packed with silica gel 100 (eluant: chloroform/methanol; 3:1), yielding 0.04 g monoester and 0.02 g diacid.

The monoester was utilized for measuring the properties in solution, whereas the diacid was immobilized on aminocellulose according to the process set forth below and measured in a sensor, as will be described below.

Preparation of an $Na^+$-, $K^+$-sensitive layer for use in a sensor:

0.03 mequ. of the diacid indicator, 0.06 g (0.3 mmol) N,N-dicyclohexyl-1,3-carbodiimide, 0.04 g (0.3 mmol) N-hydroxysuccinimide and 0.5 g activated cellulose (prepared in accordance with SU-A - 1,028,677, CA 99:177723h) were suspended in 2 ml dimethylformamide for 20 hours. The cellulose was then filtered off, washed 5 times with 5 ml dimethylformamide, 5 ml water, twice with 5 ml 0.2 n HCl, 5 ml water, twice with 5 ml 0.2 n NaOH, 10 times with 5 ml water, twice with 5 ml acetone and twice with 5 ml ether, and was dried for 16 hours at room temperature. Subsequently, the cellulose was sieved (25 μm).

Sensor discs were produced in the following manner:

0.25 g sieved (25 μm) aminocellulose fibers with an immobilized indicator were suspended in 4.75 g 10% hydrogel D4 (Tyndale Plains-Hunter LTD. Ringoes, N.J. 08551) in 90% ethanol-water for 16 hours. The resulting homogenous dispersion was applied to a polyester foil (Goodfellow; Cambridge; Prod. No. LS 146585) up to a dry density of 10 μm. This foil was coated over with 3% activated carbon in 10% D4 hydrogel up to a dry density of 5 μm, whereupon a small disc 2.5 cm in diameter was cut out. This disc was left in the buffer for at least 16 hours for activation.

A method of cutting and measuring sensor discs was described by M. J. P. Leiner and P. Hartmann in Sensors and Actuators B, 11 (1993), 281–289 ("Theory and Practice in optical pH sensing").

Figure 3:
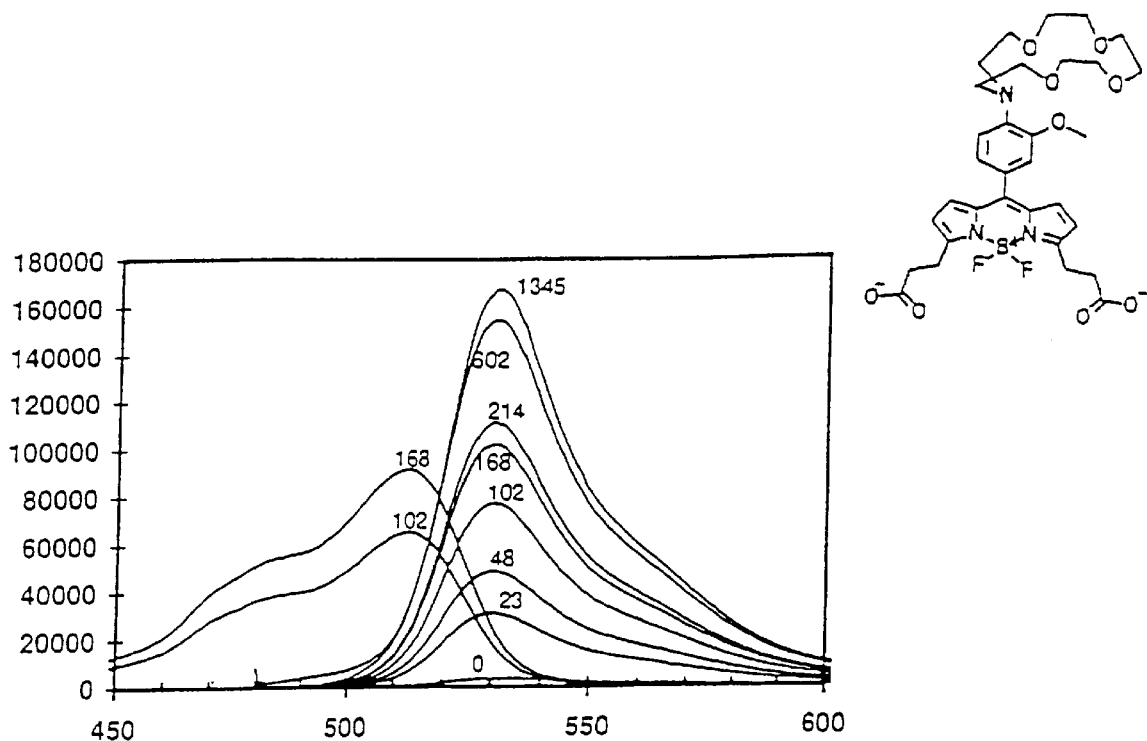
FIG. 3 is a graph illustrating the luminescence versus wavelength of a 4,4-difluoro-4-bora-3a,4a-diaza-s-indacene compound wherein $R_7$ the ionophoric moiety is a $Na^+$ sensitive monoaza-crown ether moiety in accordance with the invention.
Figure 4:
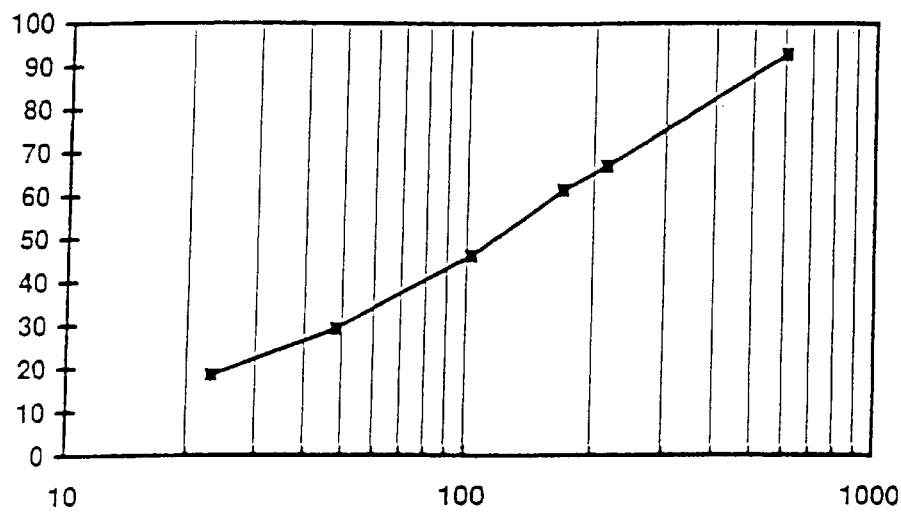
FIG. 4 is a graph illustrating the luminescence properties versus concentration of sodium ions of a 4,4-difluoro-4-bora-3a, 4a-diaza-s-indacene derivative wherein the ionophoric moiety is a monoaza-crown ether in accordance with the invention.

3. Luminescence properties of some compounds of the invention:

FIGS. 3 and 4 show the luminescence properties of two indicators of the invention as a function of the given concentration of alkali ions. The ordinates of the illustrated diagrams give the relative luminescence intensities.

3.1. FIG. 3: 4,4-difluoro-4-bora-3a,4a-diaza-s-indacene derivative (general Formula I, with $R_7$=aza-crown as the $Na^+$-sensitive, ionophoric moiety; $R_2$, $R_3$, $R_5$ and $R_6$=H; $R_1$ and $R_4$=—$CH_2$—$CH_2$—COO—)

Using the above derivative, a sensor disc was prepared, and the alkali-ion-dependent luminescence intensity was measured in a set-up described by M. J. P. Leiner and P. Hartmann in Sensors and Actuators B 11; 281–289, 1993.

Figure 5:
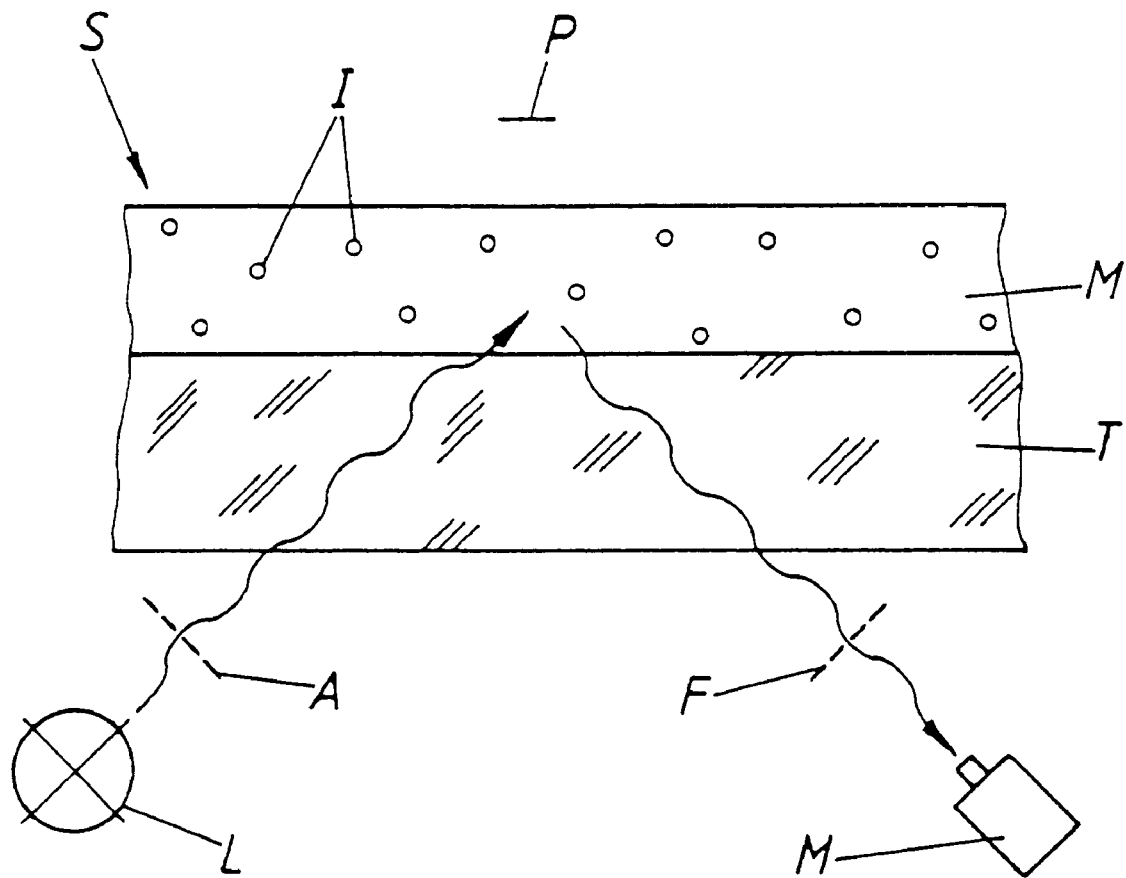
FIG. 5 is a schematic of a luminescence measuring system in accordance with the invention.

The measuring set-up is represented schematically in FIG. 5, where S denotes a portion of the sensor disc. The compound dissolved in the hydrophilic ion-permeable polymer (hydrogel) is denoted by I. This layer M is carried by a carrier T permeable to excitation and measuring radiation, which is a transparent foil.

According to the invention, the compound I can also be bound to the ion-permeable matrix directly in a covalent manner or it can be present in the matrix in physically dissolved condition.

For measurement, the sensor disc was introduced into a thermostatted through-flow cell impervious to light and was contacted with samples P having different concentrations of alkali ions.

The optical measuring system consisted of a blue LED as the light source A, a photodiode M as the detector, optical filters A and F for selecting the wavelengths, a fiber-optic arrangement for conducting the excitation light into the polymer M and for conducting the emission light to the photodetector M as well as a device for electronic signal processing (not illustrated). At the excitation end there was utilized an interference filter (peak transmission at 480 nm) and at the emission end a 520 nm cut-off filter.

The abovementioned derivative was dissolved in a buffer (tris(hydroxymethyl)aminomethane/HCl; pH: 7.4) in a concentration of $2\times10^{-5}$ mol/l as an $Na^+$ indicator. To aliquots of this solution, different quantities of NaCl were added to obtain concentrations of sodium ions of 0, 23, 48, 102, 168, 214 and 1345 mmol/l Na.

In all cases, the excitation/emission spectra were determined by means of a commercial spectrofluorometer.

3.2. FIG. 4: 4,4-difluoro-4-bora-3a,4a-diaza-s-indacene derivative (general Formula I, with $R_7$=aza-crown as the $Na^+$-sensitive, ionophoric moiety; $R_2$, $R_3$, $R_5$ and $R_6$=H; $R_1$ and $R_4$=—$CH_2$—$CH_2$—COO—NH-polymer)

In accordance with the above method a sensor disc was prepared using the abovementioned compound, said disc having an $Na^+$-sensitive layer, with the $Na^+$ indicator being covalently immobilized on amminocellulose.

FIG. 4 shows the relative luminescence intensity (ordinate) as a function of the concentration of sodium ions (logarithmic scale).

The measuring medium was 30 mmol/l tris/HCl buffer, $CO_2$-free; pH: 7.4; 37° C.

We claim:

1. Compound having the general Formula I

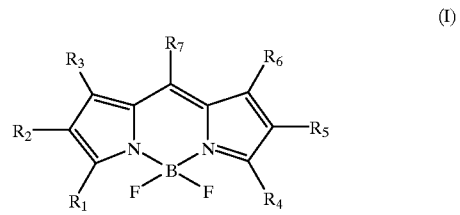

wherein one of the groups $R_1$, $R_2$, $R_3$, $R_4$, $R_5$, $R_6$, and $R_7$ represents an ionophoric moiety and the remaining groups each independently are hydrogen, a lipophilic or hydrophilic group or a reactive group for coupling to a polymer or a biomolecule, or $R_2$ forms an aromatic ring system together with $R_3$ and $R_5$ forms an aromatic ring system together with $R_6$ wherein the ionophoric moiety is a monoaza-crown ether having the general Formula II

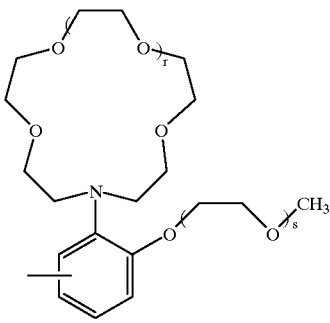

(II)

in which r and s independently is one selected from the group consisting of 0, 1 or 2.

2. Compound according to claim 1, wherein $R_7$ is an ionophoric moiety and $R_3$ and $R_6$ are independently hydrogen or methyl.

3. Compound according to any one of claim 1 or claim 2, wherein $R_1$ and $R_4$ each are a lipophilic group.

4. Compound according to claim 1 wherein r is 1 and s is 0.

5. Compound according to claim 1 wherein r is 2 and s is 1.

6. Compound according to claim 3 wherein $R_1$ and $R_4$ are each a tertiary butyl group.

7. Method for detecting sodium ions in a sample comprising the steps of:

contacting the sample with a luminescence indicator comprising a compound according to claim 5;

measuring the luminescence of the luminescence indicator; and detecting the presence of sodium in the sample based on the measured luminescence.

8. Method for detecting potassium ions in a sample comprising the steps of:

contacting the sample with a luminescence indicator comprising a compound according to claim 5;

measuring the luminescence of the luminescence indicator; and detecting the presence of potassium in the sample based on the measured luminescence.

* * * * *

UNITED STATES PATENT AND TRADEMARK OFFICE
CERTIFICATE OF CORRECTION

PATENT NO. : 5,981,746

DATED : November 9, 1999

INVENTOR(S) : Wolfbeis et al.

It is certified that error appears in the above-identified patent and that said Letters Patent is hereby corrected as shown below:

On the Title Page:

[56] References Cited: Insert before "OTHER PUBLICATIONS":
-- FOREIGN PATENT DOCUMENTS
1028677 ........ Soviet Union --

Column 1, line 30: "sb" should read --so--;.

Column 2, line 13 "f.i" should read --e.g.--;

Column 2, line 46 "f.i." should read --e.g--;

Column 2, line 52 "f.i." should read --e.g.--;

Column 2, line 54 "f.i." should read --e.g.--;

Column 2, line 55 "f.i." should read --e.g.--;

Column 2, line 56 "f.i." should read --e.g.--;

Column 4, line 13 "is" should read --are--;

Column 4, line 18 "man" should read --many--;

Column 4, line 25 "f.i." should read --e.g.--;

Column 5, line 43 "(308 mml)" should read --(308 mmol)--;

UNITED STATES PATENT AND TRADEMARK OFFICE
CERTIFICATE OF CORRECTION

PATENT NO. : 5,981,746

DATED : November 9, 1999

INVENTOR(S) : Wolfbeis et al.

It is certified that error appears in the above-identified patent and that said Letters Patent is hereby corrected as shown below:

Column 6, line 7 "D 12." should read --D12.--;

Column 6, line 48 "f.i." should read --e.g.--; and

Column 7, line 33 "mequ." should read --meq--;

Signed and Sealed this

Tenth Day of April, 2001

Attest:

NICHOLAS P. GODICI

Attesting Officer    Acting Director of the United States Patent and Trademark Office